United States Patent [19]
Vain

[11] Patent Number: 6,132,385
[45] Date of Patent: Oct. 17, 2000

[54] METHOD AND A DEVICE FOR RECORDING MECHANICAL OSCILLATIONS IN SOFT BIOLOGICAL TISSUES

[75] Inventor: Arved Vain, Tartu, Estonia

[73] Assignee: University of Tartu, Tartu, Estonia

[21] Appl. No.: 09/155,219

[22] PCT Filed: Mar. 21, 1997

[86] PCT No.: PCT/EE97/00001

§ 371 Date: Sep. 24, 1998

§ 102(e) Date: Sep. 24, 1998

[87] PCT Pub. No.: WO97/35521

PCT Pub. Date: Oct. 2, 1997

[30] Foreign Application Priority Data

Mar. 27, 1996 [EE] Estonia .................................. P9600015

[51] Int. Cl.$^7$ .................................................. A61B 19/00
[52] U.S. Cl. ............................................................ 600/553
[58] Field of Search ............................ 600/553; 128/782, 128/739

[56] References Cited

U.S. PATENT DOCUMENTS

| | | | |
|---|---|---|---|
| 3,200,814 | 8/1965 | Taylor et al. | 600/553 |
| 5,195,532 | 3/1993 | Schumacher et al. | 128/739 |
| 5,471,996 | 12/1995 | Boatright et al. | 128/782 |

FOREIGN PATENT DOCUMENTS

| | | |
|---|---|---|
| 2359411 | 2/1978 | France . |
| 1782537 | 12/1992 | U.S.S.R. . |
| WO 86/03393 | 6/1986 | WIPO . |

OTHER PUBLICATIONS

Daly et al., IEEE Proceedings of the 23$^{rd}$ Annual Conference on Engineering in Medicine and Biology, "Clinical Applications of Mechanical Impedance Measurements on Human Skin," Nov. 16, 1970, Washington D.C., U.S.

International Search Report for International Application No. PCT/EE97/00001 dated Jul. 11, 1997.

*Primary Examiner*—Max Hindenburg
*Assistant Examiner*—Brian Szmal
*Attorney, Agent, or Firm*—Reed Smith Shaw & McClay LLP

[57] ABSTRACT

The method and device for recording mechanical oscillations in soft biological tissues consists of the following: biological tissue is mechanically influenced by means of the testing end (6) of the device and its mechanical responses are subsequently recorded as a graph representing the evoked oscillations. Prior to that, an inflexible plane means (12) is fastened onto the biological tissue in order to designate the area under investigation and connect the testing end with the tissue, causing no harm to the latter. After that the testing end will be inflexibly connected with the inflexible plane means for the time period it takes to influence the tissue mechanically and record its mechanical response. The device consists of a frame (1), a pivotable double-armed lever (2), an electromechanical transducer (3), a shutter (4), a grip, an electromechanical pickup (5), a testing end (6), a pivot (7), a testing end driver (8, 9), a control switch (11), a control panel (10), and an inflexible plane means (12) for marking on the tissue the area under investigation and for connecting the testing end with the tissue permanently and inflexibly, causing no harm to the biological tissue. The length of the testing end (6) is adjustable by means of, for instance, a bayonet joint.

4 Claims, 2 Drawing Sheets

METHOD AND A DEVICE FOR RECORDING MECHANICAL OSCILLATIONS IN SOFT BIOLOGICAL TISSUES

TECHNICAL FIELD

The present invention relates to medical diagnostics devices and is intended for repeated non-invasive monitoring of mechanical properties of soft biological tissues. The method and device are used to assess the efficiency of massage procedures and the effect of physiotherapeutic treatment on biological tissues, to assess quantitatively the extent of pathological processes, to determine the genetic characteristics of organs, to monitor the tone of biological tissues undergoing surgical operations, to estimate the condition of soft tissues in accordance with the needs of forensic medicine, including measurements on the scene of accident.

BACKGROUND ART

The reasons for using the mechanical properties of soft biological tissues as a source of information for assessing the functional state of tissues and organs are the following:

The intensity of metabolic processes taking place in biological tissues depends on both the internal and external environmental influences, which bring about changes in the mechanical properties of the tissues.

Physical activity, for example, causes hypertrophy of skeletal muscles, whereas inactivity causes atrophy. As a result of various neurological diseases and traumas the muscular tone undergoes significant changes. The muscular tone is characterized by means of the stiffness and dempferity properties of muscles. The stiffness depends on the intramuscular pressure, whereas the dempferity varies according to elasticity properties of the morphological structures of muscles. The human support-motor system has developed in such a way that the rotation process of a body part round the axis of a joint always has two antagonistic muscle groups involved. The agonists create a torque in relation to the axis of the joint, which is necessary for initiating the motion, while at the same time the agonists are stretched. From the point of view of movement energetics and moving in general it is important what amount of mechanical energy is needed to stretch the antagonists. This mechanical energy in its turn comprises two parts: first, the constraining force which depends on the antagonist's tonicity, the area of its cross-section, and its change in length, and second, the resisting force, caused by the dempferity properties of the antagonist with the same change in length, which depends on the velocity of stretching. On the one hand, the tone of skeletal muscles depends on the intensity of efferent innervation, on the other, on the cellular tone. The co-influence of both can cause an increase in the mechanical tension of the envelopes or facias of the organs. The elasticity of the collagen fibres of muscle envelopes in its turn affects the ability of biological tissues to dissipate mechanical energy.

Thus changes in the mechanical properties of biological tissues can cause traumas or pathological processes. At the same time, data about changes in the mechanical properties of skeletal muscles enable us to estimate the efficiency of surgical operations, physiotherapeutic procedures, massage, rehabilitation gymnastics and drug treatment.

From what was said above we can conclude that the mechanical properties of biological tissues can yield important information about the functional ability of the tissues, thus making it possible to predict the results concurrent with changes in the mechanical properties of biological tissues.

Various devices and methods have been developed for ascertaining the mechanical properties of soft biological tissues.

The common disadvantage of the methods used until now has been that either these methods themselves cause changes to the mechanical properties of the tissue under investigation or the measuring procedure lasts so long that the subject under investigation manages to change the mechanical properties of the tissue voluntarily during the procedure. Take for instance the device for measuring muscular tone which includes two cuffs. Upon one cuff an acceleration transducer is attached, while on the other cuff the mechanical impacts are produced (Author's certificate of the USSR No. 150573, A 61B 5/05, Fedorov V. L., Talysev F. M. 1961). In this case the cuff fastening causes the amount of blood in the muscle to increase, which brings about corresponding changes in the muscular tone. The results of measurements depend on how long the cuffs have been fastened to the muscle.

From among the known methods for measuring the mechanical properties of soft biological tissues, the one most similar to the present invention is the so-called method of damping oscillations, the essence of which lies in subjecting the biological tissue under investigation to external mechanical impact and subsequently recording the mechanical response of the tissue as a graph of its damping oscillations (Fenn W. G., Garwey P. H., J. Clin., Invest. 1934, 13, Pp. 383–397; Vajn A., Metod zatuhajuscih kolebanij pri diagnostike funkcional'nogo sostojanija skeletnyh mysc. Sb. naucnyh trudov. Metody vibracionnoj diagnostiki reologiceskih harakteristik mjagkih materialov i biologiceskih tkanej.—Gorkij, 1989. Pp. 116–125.).

Several devices have been designed and constructed with the aim of using the method of damping oscillations, however, due to inadequacies in their construction the results of measurements have been metrologically unreliable. The main shortcomings have been the unstable construction of the mechanism used for producing the mechanical impact to the biological tissue and deficiencies of the system used for recording the mechanical response of the biological tissue to the influence. The graph of the recorded damping oscillations obtained by means of these devices either included additional information about the elasticity of the parts of the device itself, or the signal of the device was too weak to provide metrologically reliable data about the characteristics of the mechanical properties of the biological tissues investigated.

A method and a device have been invented for non-invasive ultrasonic monitoring of the fluctuations of the properties of living tissue related to its viscoelasticity (U.S. Pat. No 4,580,574, A 61 B 10/00, B. Gavish, 1986). There is also another device for measuring the mechanical properties of soft biological tissues. (Author's Certificate of the USSR No. 1517939, A 61 B 5/10, Godin E. A., Cernys V. A. and Stengol'd E. S., 1988).

The common shortcomings of the above-mentioned two are that during the measuring procedure the subject under investigation can voluntarily change the muscular tone, since during the measuring procedure the subject is in a fixed permanent connection with the measuring apparatus; b) the fixed position of peripheral biological tissues in the measuring apparatus sets certain limitations to the possibilities of carrying out a test; c) repeated measurements provide a low level of accuracy.

Of all the known devices, the one closest in design to the present invention is the device for measuring biomechanical characteristics of biological tissues (Author's Certificate of the USSR No. 1782537, A 61 B 5/05, G 01 N 3/30, A. Vain, L.-H. Humal, 1992). The device consists of a gripped frame, into which a pivoting two-shouldered lever is attached. To the end of one shoulder two electromechanical transducers and a wheel-shaped testing end are fastened, and to the end of the other shoulder the drive of the testing end together with its controller. The device is equipped with an elastic element situated between the frame and the two-shouldered lever, and a recorder.

Among the deficiencies of the prototype first of all the presence of the same above-mentioned elastic element must be mentioned, which sets certain limits to the recording of such oscillation frequencies which are lower than the oscillation frequency of the above-mentioned elastic element, thus making signal processing more complicated, which reduces the accuracy of measurements. Also it is difficult to find for the elastic element of the device an elastic material with such stable mechanical properties which would last for a long exploitation period.

Secondly, in case an elastic element is used it is important to what extent the elastic element has been deformed before the mechanical impulse is produced by the drive of the testing end. In case the deformation of the elastic element as well as the force used to create the initial pressure of the testing end against the biological tissue are of a small order, and the mechanical impulse created by the drive is of a relatively great magnitude, the testing end may lose its contact with the biological tissue under investigation during the oscillation process after the switch-off of the drive of the testing end. So, as a consequence of systematic errors, the resulting graph of oscillations and its analysis will become valueless.

Thirdly, it has been established that in case the initial pressure of the elastic element is of a relatively great magnitude, then the mechanical impulse produced by the drive of the testing end can neither cause any significant deformation of the biological tissue nor evoke any noticeable damping oscillations when the drive of the testing end is switched off after the mechanical impulse has been performed. In addition to this, the creepability and relaxation properties of biological tissues will further complicate the measuring procedure and reduce its accuracy, when the initial pressure of a great magnitude is used.

DISCLOSURE OF INVENTION

The aim of the present invention is to present a method and a device for recording oscillations of soft biological tissues, so that the resulting graph of oscillations of the biological tissue under investigation would make it possible to calculate the characteristics of the mechanical properties of the biological tissue, to increase the accuracy of the measuring process, to increase the field of possible applications, to shorten the time period necessary for testing and to raise the accuracy of the measurement data (repeatability). The present invention makes it possible to carry out the monitoring of a soft biological tissue repeatedly, in an undisturbed and non-invasive way.

The essence of the present method lies in the following: the biological tissue under investigation is externally mechanically influenced by means of the testing end of the device and the mechanical response of the above-mentioned tissue is subsequently recorded as a graph representing the evoked oscillations of the tissue. But before exerting the above-mentioned external mechanical impact by the testing end of the device, as distinct from any other known methods, an inflexible plane means—joining marker—is fastened onto the biological tissue in order to designate the area under investigation and connect the testing end with the tissue without causing any harm to the latter. After that the testing end is inflexibly connected to the inflexible plane means for the time it takes to influence the tissue mechanically and register its mechanical response.

The device for recording the oscillations of soft biological tissues—myometer—consists of a supplementary inflexible plane means for designating the surface area of the soft biological tissue under investigation and for providing an inflexible continuous connection of the testing end of the myometer with the soft biological tissue under investigation without harming the tissue. The length of the testing end is adjustable by means of, for instance, a bayonet joint. The mass of the testing end does not change during the adjustment process.

BRIEF DESCRIPTIONS OF DRAWINGS

FIG. 1

Figure 1:
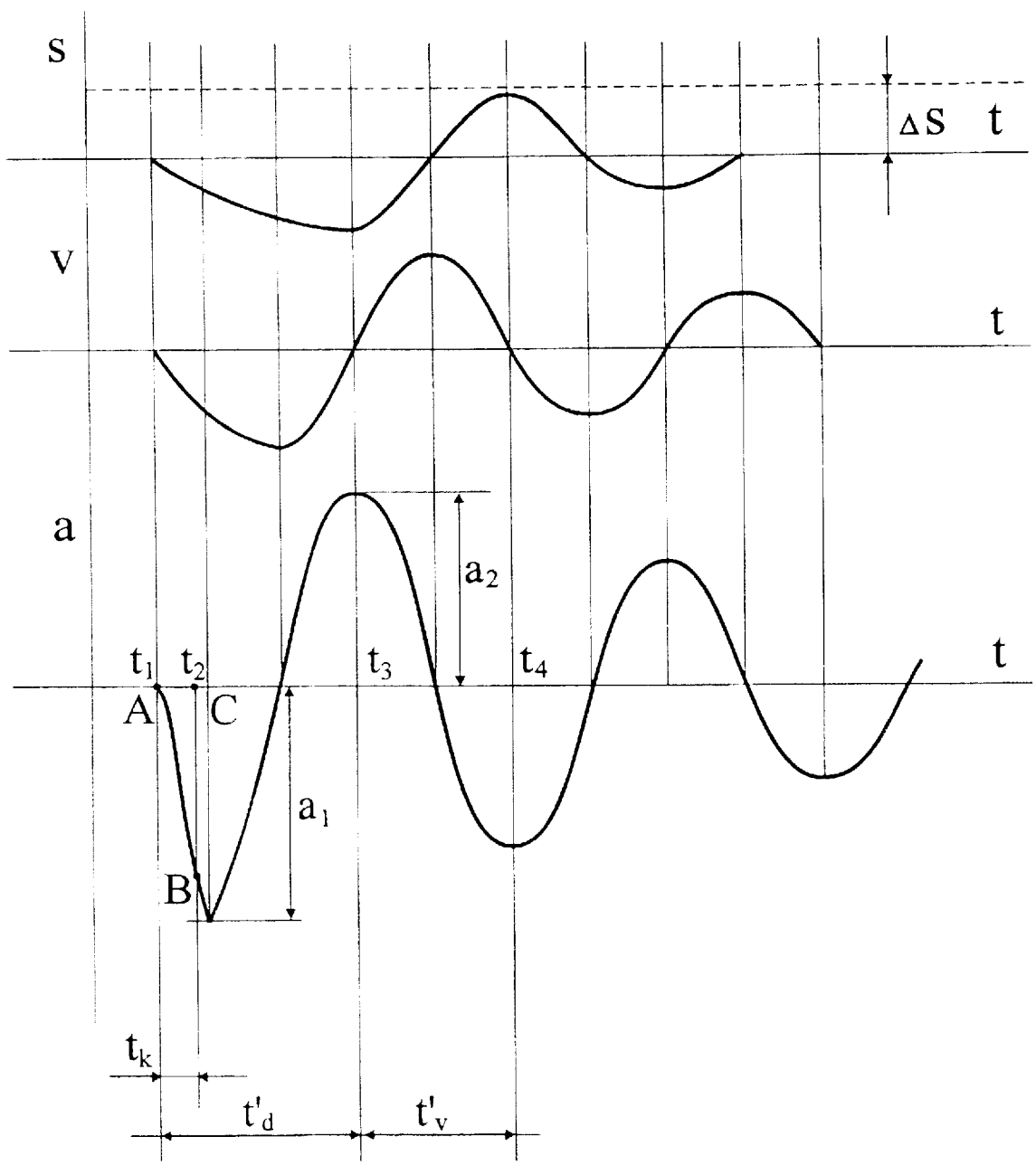
FIG. 1 is a graph of damping oscillations of soft biological tissue.

$t_1$—time, denoting the initial moment of the mechanical impact on the tissue, produced by the testing end drive;

$t_2$—time, when the testing end drive is switched off and the biological tissue begins to oscillate;

$t_3$—initial moment of the mechanical influencing of the biological tissue caused by the force of elastic deformation of the biological tissue on the testing end;

$t_4$—the stoppage of upward movement of the testing end, the initial moment of the second period of the oscillation;

$t_k$—working cycle of the testing end drive;

$t'_d$—duration of the first mechanical influence on the soft biological tissue;

$t'_v$—time during which the soft biological tissue restores its initial shape after the first deformation caused by the first mechanical influence;

$a_1$—peak acceleration caused by the mechanical influence on the soft biological tissue;

$a_2$—peak acceleration of the testing end emerging as a result of the force of elasticity of the soft biological tissue, evoked by the mechanical influence on the tissue;

v—graph of the velocity of the testing end;

s—trajectory of the testing end;

Δs—static deformation of the soft biological tissue, caused by the weight of the testing end.

The area ABC is equal to the deformation velocity of the soft biological tissue $v_d$.

BEST MODE FOR CARRYING OUT THE METHOD

At first it is established by way of palpation which area of the biological tissue under investigation is most convenient for testing, e.g. a tendon of a peripheral muscle. Before exerting external mechanical influence onto the biological tissue an inflexible plane means—joining marker—is attached to the surface of the above-mentioned area (by means of, e.g., vacuum, adhesive or some other binding) for marking on the surface of the biological tissue the area under investigation and for connecting the testing end to the tissue without harming the biological tissue. After that the testing end of the device is connected inflexibly to the above-mentioned joining marker for the time necessary for producing an external mechanical influence and recording the mechanical response of the biological tissue. To connect the testing end with the joining marker, adhesive, vacuum or some other mechanical coupling is used. On the area to which the joining marker is attached, an external mechanical influence is exerted by means of the testing end of the device. After delivering the external force impulse, the testing end will maintain its inflexible connection with the joining marker as well as with the area of the soft biological tissue under investigation, repeating the oscillations of the soft biological tissue in the process of restoring the situation before its elastic deformation. When the measuring procedure is terminated, the testing end is disconnected from the joining marker. To perform measurements on the next area under investigation, the testing end is connected to the next joining marker. The measuring procedure described above is of short duration, and therefore neither affects the metabolic processes of the tissues under investigation nor causes neurological reactions of the subject under investigation. When the measuring procedure is terminated, the joining markers can be removed.

The graph of damping oscillations of a soft biological tissue, recorded by means of the method described above will contain valuable information, on the basis of which the characteristics of the mechanical properties of the tissue can be calculated, e.g. the oscillation period and the measure of damping of the oscillation, its logarithmic decrement, etc.

BEST MODE FOR CARRYING OUT THE DEVICE

Figure 2:
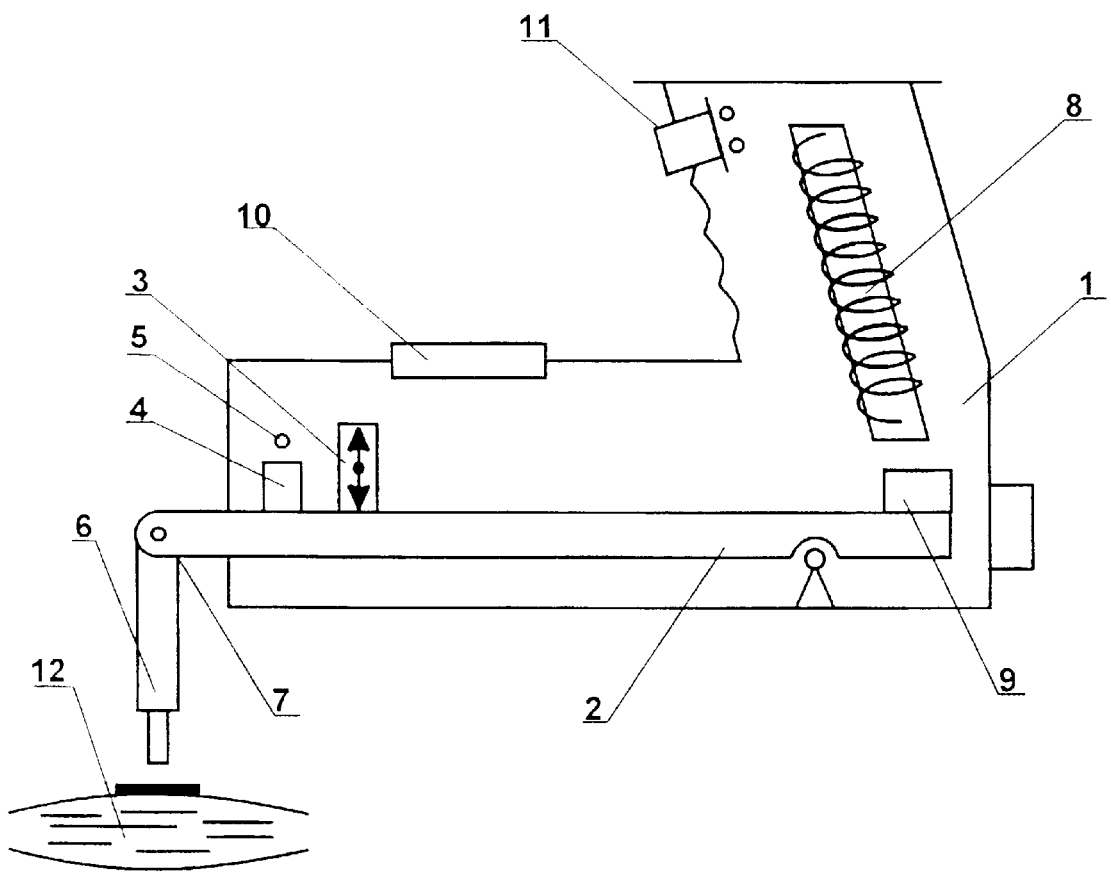
FIG. 2 is a view of the device for recording the oscillations of soft biological tissues—the myometer.

The device for recording the oscillations of soft biological tissues, FIG. 2, includes the frame 1 with the grip, the pivotable double-armed lever 2 together with the electromechanical transducer 3, the shutter 4, the electromechanical pickup 5, the testing end 6, the pivot 7, the drive of the testing end, which includes the solenoid 8 and the armature 9, the control panel 10, the switch 11 for controlling the measurement process and the inflexible plane means for marking on the tissue the area under investigation and for establishing a permanent and inflexible connection of the testing end with the tissue under investigation—the joining marker 12.

Holding the device by its grip, the investigator places the striking end 6 on the joining marker 12, previously attached to the biological tissue by means of, e.g., adhesive, vacuum or some other mechanical coupling. After pressing the switch 11 the shutter 4 is moved close to the electromechanical pickup 5 by turning the frame of the device. When the shutter 4 covers the electromechanical pickup 5, the electric current is switched on to the solenoid 8 for a previously fixed time period and during this time period the armature 9 is pulled into the solenoid 8 by its electromagnetic field, in result of which the testing end exerts to the tissue under investigation a mechanical impact through the joining marker. When the above-mentioned time period ends, the testing end drive is switched off and the biological tissue together with the joining marker and the testing end perform damping oscillations, the characteristics of which are dependent on the elasticity properties of the soft biological tissue under investigation. The oscillations are recorded and the necessary mechanical characteristics of the tissue are calculated, the variant of calculations is indicated on the control panel 10 designed as a numerical indicator. After pressing the switch 11 the initial state of the device is restored and the procedure can be repeated immediately. The measuring procedure can be completely computer-controlled. This makes it possible to record the oscillations of biological tissues quickly and repeatedly.

The length of the testing end 6 is adjustable by means of, for instance, a bayonet joint. The mass of the testing end does not change during the adjustment process.

The measurements are presented by the graph of damping oscillations of the biological tissue under investigation, which reflects the nature of the short-time (some ms duration) deformation of the tissue (the mechanical characteristics of the deformation) and the nature of the subsequent oscillation of the biological tissue under investigation (which includes such mechanical characteristics as the stiffness and the dempferity properties). It takes the computer-controlled device not more than 0.5 seconds to produce one complete oscillation graph, after that the device is ready for repeating the measuring procedure.

The application of the method and device described above makes it possible

- to increase the accuracy of the measuring procedure, replacing the elastic element used in the construction of the prototype by a non-invasive inflexible connection of the testing end to the area of the soft biological tissue under investigation, using the joining marker described above;
- to measure the characteristics of the soft biological tissue under investigation in optional position of the tissue;
- to expand the field of applications of the device using the possibility to change the length and position of the testing end;
- as a result of the soft biological tissue under investigation being inflexibly connected with the testing end of the device, to use a wide range of deformation velocities of the tissues, without any pain sensations to the subject or changes in blood circulation of the tissues under investigation, at the same time the stability and lack of distortions of the resulting oscillation graphs is secured by the permanent contact of the testing end with the tissue under investigation;
- to shorten the testing time by previously fastening the necessary amount of joining markers to the area of the soft biological tissue under investigation;
- to raise the accuracy of the measuring data and to guarantee repeatability of the procedure.

What is claimed is:

1. Method of recording mechanical damped natural oscillations of soft biological tissues of a tissue-bearing subject via exerting on the soft biological tissue an external mechanical impact at a testing end and subsequently recording the mechanical response of the biological tissue as a graph of damped natural oscillations of the tissue, wherein:

before exerting the external mechanical impact on the biological tissue at the testing end, an inflexible plane means is fastened onto the biological tissue in order to mark the tissue area under investigation and to facilitate the connection of the testing end with the tissue in a manner that prevents the testing end from harming the tissue, thereafter the testing end is inflexibly connected to the inflexible plane means over a duration sufficient for influencing the tissue mechanically and for recording the mechanical response of the biological tissue, and thereafter an external mechanical impact is applied to the tissue under investigation over a duration of some milliseconds, ending with rapid cessation of the impact, whereby the following are avoided:

harm to the biological tissue;

changes in metabolic processes of the tissue; and neurological reactions of the tissue under investigation.

2. A device for recording natural oscillations of soft biological tissues of a tissue-bearing subject, the device including a frame with a grip, a pivoting double-armed lever with an electromechanical transducer and shutter, all attached to the frame, an electromechanical pickup, a testing end, a testing end drive that includes a pivot, and a switch for controlling the measuring process and a recorder, wherein:

said device further comprises an inflexible plane means for marking the area under investigation and for facilitating the connection of the testing end of the device to the tissue, permanently and inflexibly, in a manner that avoids causing:
harm to the biological tissue;
changes in metabolic processes of the tissue; and
neurological reactions of the tissue-bearing subject under investigation; and said device is adapted to measure said natural oscillations in the absence of voluntary muscular contraction in the tissue-bearing subject.

3. The device according to claim 2, wherein the length of the testing end is adjustable, said device further comprising an element for ensuring that the mass of the testing end remains constant during adjustment.

4. The device according to claim 3, wherein said element comprises a bayonet joint.

* * * * *